US00PP22111P2

(12) United States Plant Patent
Kraan

(10) Patent No.: US PP22,111 P2
(45) Date of Patent: Sep. 6, 2011

(54) ***HYDRANGEA* PLANT NAMED 'BOKRAFLAME'**

(50) Latin Name: *Hydrangea paniculata*
Varietal Denomination: Bokraflame

(75) Inventor: Kees Jan Kraan, Papenveer (NL)

(73) Assignee: Boot & Co Boomkwekerijen BV, Boskoop (NL)

( * ) Notice: Subject to any disclaimer, the term of this patent is extended or adjusted under 35 U.S.C. 154(b) by 0 days.

(21) Appl. No.: 12/653,994

(22) Filed: Dec. 22, 2009

(51) Int. Cl.
*A01H 5/00* (2006.01)

(52) U.S. Cl. ..... Plt./250

(58) Field of Classification Search ..... Plt./250
See application file for complete search history.

(56) References Cited

PUBLICATIONS

Upov-rom Plant Variety Database 2010/06. Citation for *Hydrangea* 'Bokraflame', one page.*

* cited by examiner

*Primary Examiner* — June Hwu
(74) *Attorney, Agent, or Firm* — Mark P. Bourgeois

(57) ABSTRACT

A new cultivar of *Hydrangea* plant named 'Bokraflame' that is characterized by a compact habit, dense broad conical flower panicles with large numbers of sterile flowers and green-white sterile flower sepals that fade to grey-red.

1 Drawing Sheet

Botanical classification: *Hydrangea paniculata.*
Variety denomination: 'Bokraflame'.

BACKGROUND OF THE INVENTION

The present invention relates to a new and distinct cultivar of *Hydrangea* plant botanically known as *Hydrangea paniculata* and hereinafter referred to by the cultivar name 'Bokraflame'.

The new cultivar is the product of a breeding program conducted by the inventor in a cultivated area of Boskoop, The Netherlands. The objective of the breeding program was to develop new *Hydrangea* cultivars with a compact habit and attractive flowers.

'Bokraflame' originated from open pollination of the female or seed parent an unnamed proprietary cultivar of *Hydrangea paniculata* (not patented) in 2003. The male or pollen parent is unknown. The cultivar 'Bokraflame' was selected by the inventor in 2006 as a single plant in Boskoop, The Netherlands.

Asexual reproduction by cuttings of the new cultivar 'Bokraflame' was first performed in 2006 in Boskoop, The Netherlands. Since that time, under careful observation, the unique characteristics of the new *Hydrangea* cultivar have been uniform, stable and reproduced true to type in successive generations of asexual reproduction.

SUMMARY OF THE INVENTION

The following represent the distinguishing characteristics of the new *Hydrangea* cultivar 'Bokraflame'. These traits in combination distinguish 'Bokraflame' as a new and distinct cultivar apart from all other existing varieties of *Hydrangea* known to the inventor. 'Bokraflame' has not been tested under all possible conditions and phenotypic differences may be observed with variations in environmental, climatic, and cultural conditions, however, without any variance in genotype.

1. *Hydrangea* 'Bokraflame' exhibits a compact habit.
2. *Hydrangea* 'Bokraflame' exhibits dense broad conical flower panicles with large numbers of sterile flowers.
3. *Hydrangea* 'Bokraflame' exhibits green-white sterile flower sepals that fade to grey-red.

The closest comparison plant is *Hydrangea* 'Limelight' (U.S. Plant Pat. No. 12,874) 'Bokraflame' is distinguishable from 'Limelight' in having a more compact habit and sterile flowers that are green-white. The sterile flowers of 'Limelight' are yellow-white. The sterile flower sepals of 'Bokraflame' fade to grey-red. The sterile flower sepals of 'Limelight' fade to light pink.

The new cultivar 'Bokraflame' is distinguishable from the unnamed female parent in having a more compact habit and a larger number of sterile flowers. The sterile flower sepals of 'Bokraflame' fade to grey-red. The sterile flower sepals of the unnamed female parent plant fade to dark pink.

BRIEF DESCRIPTION OF THE DRAWING

The accompanying photograph illustrates the distinguishing traits of *Hydrangea* 'Bokraflame'. The plant in the photograph shows an overall view of a two year old outdoor field grown plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Hydrangea* cultivar named 'Bokraflame'. Data was collected in Boskoop, The Netherlands from two year old outdoor field grown plants. The time of year was October and the temperatures ranged from 8-20° Centigrade during the day, and 1-12° Centigrade during the night. The light level was natural outdoor light and there were no photoperiodic treatments or growth retardants used. Color determinations are in accordance with The Royal Horticultural Society Color Chart, 5th edition 2007, except where general color terms of ordinary dictionary significance are used. The growing requirements are similar to the species.

Botanical classification: *Hydrangea paniculata* 'Bokraflame'.

Parentage: 'Bokraflame' resulted from open pollination between the female parent an unnamed proprietary cultivar of *Hydrangea paniculata* and an unknown male parent.

Vigor: Moderate.

Growth rate: Moderate.

Growth habit: Broad upright.

Plant shape: Broad obovate.

Suitable container size: 2 liter.

Height: Average 63.6 cm. in height.

Width: Average 70.6 cm. in diameter.

Hardiness: USDA Zone 4.

Propagation: Softwood cuttings.

Time to initiate roots: Approximately 26 weeks are required to produce a rooted plant.

Crop time: Approximately 12 months are required to achieve a finished plant from a rooted cutting.

Root system: Fine and fibrous.

Stem:

*Branching habit.*—Free branching.

*Basal branching.*—Yes.

*Average number of lateral branches.*—27.

*Pinching.*—No.

*Lateral branch diameter.*—Average 5 mm. in diameter.

*Lateral branch length.*—Average 46.2 cm. in length.

*Stem angle.*—Average 50 degrees from soil plane.

*Stem strength.*—Strong.

*Stem color immature.*—183C.

*Stem color mature.*—N199B to 200D.

*Pubescence.*—Immature branches sparsely covered with short adpressed hairs, 0.75 mm. in length, N155A in color.

*Internode length.*—Approximately 4.9 mm. between nodes.

*Shape.*—Rounded, smooth.

Foliage:

*Leaf arrangement.*—Opposite or in whorls of three.

*Leaf shape.*—Ovate.

*Leaf tip.*—Apiculate.

*Leaf base.*—Rounded.

*Leaf margin.*—Serrate.

*Leaf length.*—10.2 cm.

*Leaf width.*—5.3 cm.

*Texture upper side.*—Dull, moderately rugose.

*Texture under side.*—Dull, slightly rugose.

*Pubescence.*—Both sides covered with short hairs, 1 mm. in length, color 157C to 157D, hairs on upper side strigose.

*Vein pattern.*—Pinnate.

*Leaf color young, upper surface.*—137B.

*Leaf color young, lower surface.*—147B.

*Leaf color mature, upper surface.*—N137A.

*Leaf color mature, lower surface.*—138B.

*Vein color, upper side.*—147B to 147C.

*Vein color, under side.*—148C to 148D.

*Leaf attachment.*—Petiolate.

*Petiole dimensions.*—5.3 cm. in length and 3.0 mm. in diameter.

*Petiole texture upper side.*—Dull, moderately pubescent with hairs 0.5 mm. in length, color 157C to 157D.

*Petiole texture under side.*—Dull, sparsely pubescent with hairs 0.5 mm. in length, color 157C to 157D.

*Petiole color upper side.*—183B.

*Petiole color under side.*—181A.

Flower:

*Flowering season.*—Summer to early autumn.

*Time to flower from planting.*—Approximately 1 year.

*Fragrance.*—None.

*Inflorescence type.*—Broad conical lacecap panicles with large sepals.

*Panicle height.*—Average 16.2 cm. in height.

*Panicle diameter.*—Average 14.3 cm. in diameter.

Sterile flowers:

*Sterile flower arrangement.*—A central eye that opens into four petals surrounded by four sepals.

*Bud length.*—Average 3.0 mm. in length.

*Bud diameter.*—Average 2.5 mm. in diameter.

*Bud shape.*—Flattened globose.

*Bud color.*—145B, tip 186B.

*Quantity of sterile flowers per inflorescence.*—Average 165.

*Aspect.*—Upright to slightly outward.

*Shape.*—Rotate.

*Dimensions.*—Average 4.2 mm. in diameter and 8.0 mm. in height.

*Longevity.*—Approximately 2 to 3 weeks.

*Persistent or self-cleaning.*—Persistent.

*Number of petals.*—Four in number.

*Petal arrangement.*—Rotate.

*Petal shape.*—Ovate.

*Petal margin.*—Entire.

*Petal apex.*—Acute.

*Petal base.*—Cuneate.

*Petal dimensions.*—Average 3.0 mm. in length and 2.0 mm. in width.

*Petal texture.*—Smooth and glossy both sides.

*Petal color when opening* (*under side*).—157C to 157D, tip 186B.

*Petal color when opening* (*upper side*).—157C to 157D, tip 186D.

*Petal color fully opened* (*under side*).—157C to 157D, tip 186B.

*Petal color fading to.*—Not fading.

*Number of sepals.*—Average 4.

*Sepal arrangement.*—Rotate.

*Sepal shape.*—Broad ovate to broad elliptic.

*Sepal margin.*—Entire.

*Sepal apex.*—Obtuse.

*Sepal base.*—Cuneate.

*Sepal dimensions.*—Average 2.1 cm. in length and 1.8 cm. in width.

*Sepal surface.*—Smooth, dull both surfaces.

*Sepal color, young* (*upper side*).—1D to 150D.

*Sepal color, young* (*under side*).—1D to 150D.

*Sepal color, mature* (*upper side*).—145B to 145C.

*Sepal color, mature* (*under side*).—145D.

*Sepal color fading to* (*upper side*).—181 C to 181 D.

*Sepal color fading to* (*under side*).—182C to 182D, base flushed with 145C.

*Pedicel dimensions.*—Average 2.2 cm. in length and 1.0 mm. in diameter.

*Pedicel angle.*—85° from vertical.

*Pedicel strength.*—Moderate.

*Pedicel texture.*—Smooth, dull.

*Pedicel color.*—155D to 157D.

*Stamen number.*—Average 8.
*Filament length.*—Average 2.5 mm.
*Filament color.*—157C to 157D.
*Anther shape.*—Double kidney shaped.
*Anther length.*—1.0 mm.
*Anther color.*—156D.
*Amount of pollen.*—Low.
*Pollen color.*—158D.
*Gynoecium.*—Absent.

Fertile flowers:
*Bud length.*—Average 3.0 mm. in length.
*Bud diameter.*—Average 2.5 mm. in diameter.
*Bud shape.*—Flattened globose.
*Bud color.*—145B, tip 186B.
*Quantity of fertile flowers per inflorescence.*—Average 120.
*Aspect.*—Upright to outward.
*Shape.*—Rotate.
*Dimensions.*—Average 5.0 mm. in diameter and 6.0 mm. in height.
*Longevity.*—Approximately 1 week.
*Persistent or self-cleaning.*—Self-cleaning.
*Number of petals.*—Five in number.
*Petal arrangement.*—Rotate.
*Petal shape.*—Ovate.
*Petal margin.*—Entire.
*Petal apex.*—Acute.
*Petal base.*—Cuneate.
*Petal dimensions.*—Average 3.0 mm. in length and 2.0 mm. in width.
*Petal texture.*—Smooth and glossy both sides.
*Petal color when opening* (*under side*).—145C.
*Petal color when opening* (*upper side*).—145C.
*Petal color fully opened* (*upper side*).—145C.
*Petal color fully opened* (*under side*).—145C.
*Petal color fading to.*—Not fading.
*Number of sepals.*—Average 5.
*Sepal arrangement.*—Rotate.
*Sepal shape.*—Broad ovate.
*Sepal margin.*—Entire.
*Sepal apex.*—Broad acute.
*Sepal base.*—Cuneate.
*Sepal dimensions.*—Average 2.0 mm. in length and 1.0 mm. in width.
*Sepal surface.*—Smooth, dull both surfaces.
*Sepal color, young* (*upper side*).—144C.
*Sepal color, young* (*under side*).—144C.
*Sepal color, mature* (*upper side*).—144C.
*Sepal color, mature* (*under side*).—144C.
*Sepal color fading to* (*upper side*).—144B.
*Sepal color fading to* (*under side*).—144B.
*Pedicel dimensions.*—Average 2.2 mm. in length and 0.5 mm. in diameter.
*Pedicel strength.*—Moderate.
*Pedicel texture.*—Smooth, dull.
*Pedicel color.*—145C.
*Stamen number.*—Average 10.
*Filament length.*—Average 3.5 mm.
*Filament color.*—155C.
*Anther shape.*—Double kidney shaped.
*Anther length.*—1.0 mm.
*Anther color.*—156D.
*Amount of pollen.*—Low.
*Pollen color.*—158D.
*Number of pistils.*—3.
*Pistil length.*—2 mm.
*Stigma shape.*—Flattened on top of style.
*Stigma color.*—145D.
*Style length.*—1.0 mm.
*Style color.*—145C.
*Ovary color.*—145A.

Fruit: Approximately 60 fruits per inflorescence are formed, which is 50% of the fertile flowers. Sterile flowers contain anthers only and do not set fruit. The fruit is a dry capsule, shaped elliptic with an attenuate base and dry remains of persistent styles on top. The average length of the fruit is 5 mm, average width of the fruit is 2 mm. Colored grey-brown to brown; N199B to 200D.

Seed: Small dust-like seeds, 0.3 mm. in size, grey-brown; N199A to N199B.

Disease and pest resistance: Has not been observed to date.

I claim:

1. A new and distinct variety of *Hydrangea* plant named 'Bokraflame' as described and illustrated.

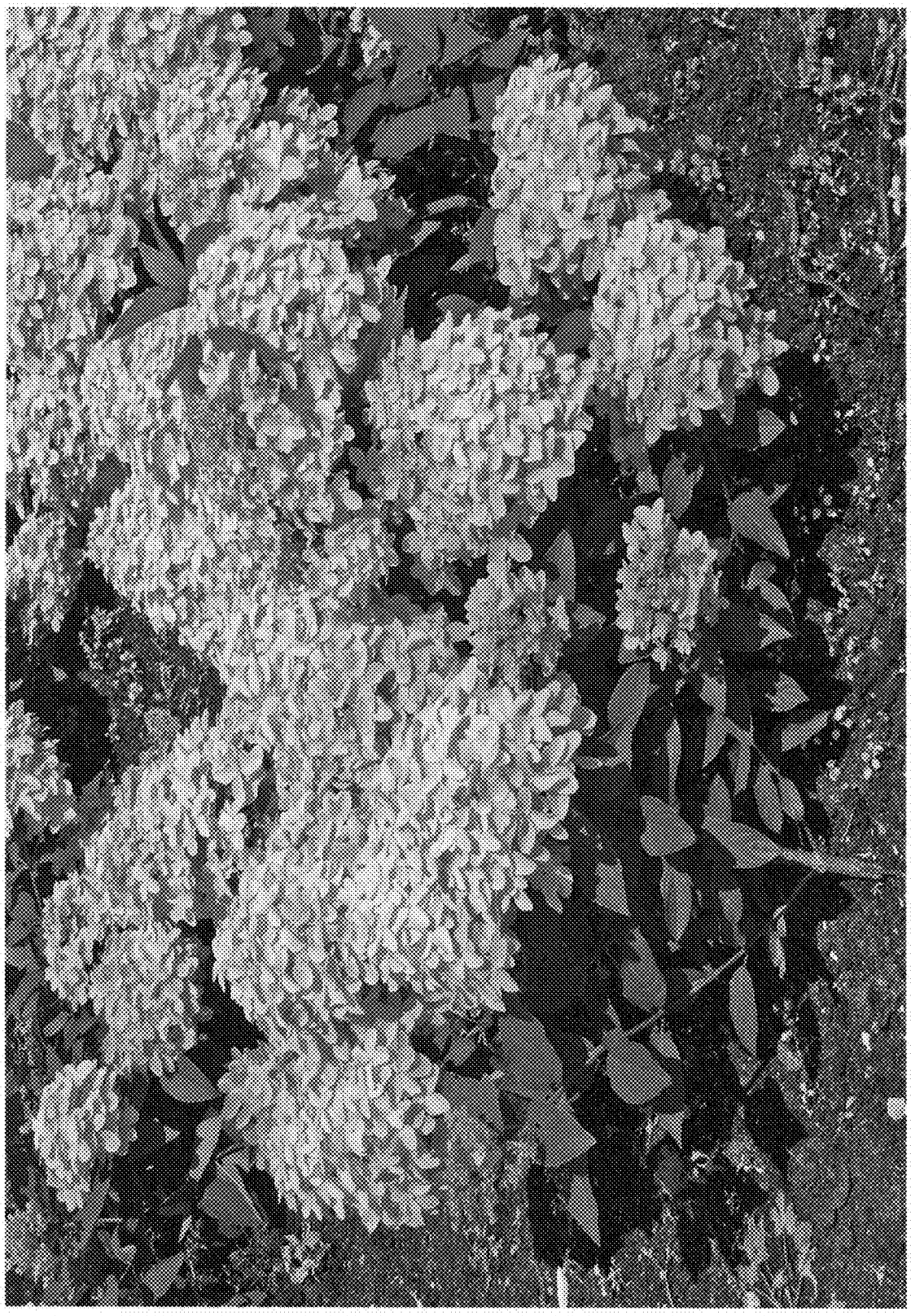

* * * * *